United States Patent
Kimura

(10) Patent No.: US 9,835,483 B2
(45) Date of Patent: Dec. 5, 2017

(54) MATERIAL TESTING MACHINE

(71) Applicant: SHIMADZU CORPORATION, Kyoto-shi, Kyoto (JP)

(72) Inventor: Motofumi Kimura, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 254 days.

(21) Appl. No.: 14/506,214

(22) Filed: Oct. 3, 2014

(65) Prior Publication Data

US 2015/0160108 A1    Jun. 11, 2015

(30) Foreign Application Priority Data

Dec. 9, 2013  (JP) ................................. 2013-254035

(51) Int. Cl.
  *G01N 3/10*    (2006.01)
  *G01F 1/34*    (2006.01)
  *G01N 3/08*    (2006.01)

(52) U.S. Cl.
  CPC ................. *G01F 1/34* (2013.01); *G01N 3/08* (2013.01); *G01N 3/10* (2013.01); *G01N 2203/0042* (2013.01)

(58) Field of Classification Search
  CPC .... G01N 3/10; G01N 2203/0042; G01N 3/08; G01F 1/34
  See application file for complete search history.

(56) References Cited

U.S. PATENT DOCUMENTS

| 2,273,152 | A | * | 2/1942 | Sonntag | G01N 3/10 137/540 |
| 4,548,296 | A | * | 10/1985 | Hasegawa | B66F 9/22 137/486 |
| 5,240,403 | A | * | 8/1993 | McAnespie | F23G 7/068 110/190 |

FOREIGN PATENT DOCUMENTS

| JP | 2011-185755 A | 9/2011 |
| JP | 2013-068492 A | 4/2013 |
| JP | 2013-72367 A | 4/2013 |

(Continued)

OTHER PUBLICATIONS

Office Action dated Nov. 24, 2016, issued in counterpart Japanese Application No. 2013-254035, with English translation (6 pages).

(Continued)

*Primary Examiner* — Laura Martin
*Assistant Examiner* — Alex Devito
(74) *Attorney, Agent, or Firm* — Westerman, Hattori, Daniels & Adrian, LLP

(57) ABSTRACT

A hydraulic pressure source includes an oil tank for storing hydraulic oil, a hydraulic pump, a motor for driving this hydraulic pump, and an inverter for changing a rotational frequency of the motor. A pipe line for drawing the hydraulic oil from the oil tank by operation of the hydraulic pump branches to a supply pipe line for supplying the hydraulic oil to the hydraulic cylinder, and a release pipe line for releasing superfluous hydraulic oil into the oil tank. The release pipe line has arranged thereon a pressure regulating mechanism and a flowmeter which measures a flow rate of the hydraulic oil flowing into the release pipe line. Based on a measurement value of the flowmeter, the inverter is operable to change the rotational frequency of the motor to become a necessary minimum rotational frequency.

10 Claims, 4 Drawing Sheets

(56) References Cited

FOREIGN PATENT DOCUMENTS

JP          2013-117404 A        6/2013

OTHER PUBLICATIONS

Third Party Information Disclosure Statement Notification dated Aug. 23, 2016, issued in counterpart Japanese Application NO. 2013-254035 with English Translation (2 pgs.).
Third Party Information Disclosure Notification dated Jan. 24, 2017, issued in counterpart Japanese Application No. 2013-254035. (2 pages).
"Shin-Shiritai Yuatsu/Kiso-hen (i.e., the new basics of hydraulic pressure you should know)", Japan Machinist Co., Ltd., ISBN 978-4-88049-040-3, Aug. 10, 2013, pp. 24-25, pp. 256-257. Concise Explanation of the Relevance: This publication explains the feature of a hydraulic device on pp. 24 to 25. This publication also explains a cooler arranged in a hydraulic circuit on pp. 256 to 257. These descriptions in this publication (particularly Figs. 1-8) appear to be relevant to the arrangement of the oil cooler recited in pending Claim 11 of the present application.

\* cited by examiner

MATERIAL TESTING MACHINE

BACKGROUND OF THE INVENTION

1. Field of the Invention

This invention relates to a material testing machine which drives a hydraulic cylinder to apply load to specimens.

2. Description of the Related Art

Generally, a material testing machine applies various loads to test pieces such as specimens by driving a loading mechanism. In the case of fatigue testing done on a specimen, for example, vibration is continuously applied to the specimen. And a hydraulic cylinder is used as the loading mechanism for applying vibration to the specimen.

In such a material testing machine that drives a hydraulic cylinder, a hydraulic pressure source including a hydraulic pump is used to supply hydraulic oil to the hydraulic cylinder. This hydraulic pressure source has a motor for driving the hydraulic pump, and a relief valve for maintaining constant a supply pressure of the hydraulic oil supplied the hydraulic cylinder during an execution of material testing.

In recent years, in order to attain power-saving, a material testing machine has been proposed which reduces power consumption by the hydraulic pressure source (see Japanese Unexamined Patent Publication No. 2011-185755). Since the power consumption by the hydraulic pressure source depends mainly on the rotational frequency of the motor for driving the hydraulic pump and the supply pressure of hydraulic oil, the material testing machine described in Japanese Unexamined Patent Publication No. 2011-185755 inhibits unnecessary power consumption by changing the rotational frequency of the motor by inverter control based on the strokes of a cylinder rod of the hydraulic cylinder.

The material testing machine described in Japanese Unexamined Patent Publication No. 2011-185755 determines, by calculation using coefficients derived from some characteristics of a hydraulic circuit, a required discharge rate from a discharge pump during a test execution or, in other words, a required flow rate of hydraulic oil flowing through a supply route from the discharge pump to the hydraulic cylinder (see Japanese Unexamined Patent Publication No. 2011-185755, paragraph [0043]). However, there can be a divergence between a required flow rate calculated and an actually required flow rate. In such a case, more electric power is consumed than is necessary.

SUMMARY OF THE INVENTION

The object of this invention, therefore, is to provide a material testing machine which improves energy efficiency of a hydraulic pressure source to be able to reduce power consumption.

The above object is fulfilled, according to this invention, by a material testing machine for conducting a material testing by applying a testing force to a test specimen, the machine comprising a hydraulic cylinder, a hydraulic pressure source for supplying hydraulic oil to the hydraulic cylinder, and a flow control valve for controlling flow rates of the hydraulic oil which flows into the hydraulic cylinder and out of the hydraulic cylinder; wherein the hydraulic pressure source includes a pump for feeding the hydraulic oil in a tank to the hydraulic cylinder; a motor for driving the pump; an inverter connected to the motor for changing a rotational frequency of the motor; a release pipe line having mounted thereon a pressure regulating mechanism for regulating a pressure in a hydraulic circuit, the release pipe line branching from a pipe line which supplies the hydraulic oil from the tank through the pump to the hydraulic cylinder, for releasing a superfluous part of the hydraulic oil discharged from the pump; a flowmeter mounted on the release pipe line for measuring a flow rate of the hydraulic oil flowing into the release pipe line; and a controller for controlling the rotational frequency of the motor through the inverter based on a measurement value of the flowmeter.

According to such material testing machine, the flowmeter is mounted on the release pipe line, and a superfluous part, not used for loading in the material testing, of the hydraulic oil discharged from the hydraulic pump is monitored with the flowmeter. The rotational frequency of the motor is changed based on this superfluous flow rate, thereby to minimize the superfluous flow rate, to improve energy efficiency of the hydraulic pressure source, and to reduce power consumption.

In one preferred embodiment, the material testing machine further comprises a displacement detector for detecting strokes of a cylinder rod of the hydraulic cylinder when conducting the material testing by applying the testing force to the test specimen; an input unit for setting beforehand the strokes of the cylinder rod of the hydraulic cylinder when conducting the material testing by applying the testing force to the test specimen; and a storage unit for storing the strokes of the cylinder rod of the hydraulic cylinder inputted by the input unit; wherein the controller is arranged to set an initial starting rotational frequency of the motor in response to whether a testing control mode selected at a time of starting the testing is a stroke control mode based on a detection value of the displacement detector or a control mode other than the stroke control mode, and when the testing control mode selected at the time of starting the testing is the stroke control mode, to start the motor at a rotational frequency according to a discharge rate of the pump calculated based on the strokes of the cylinder rod of the hydraulic cylinder stored in the storage unit.

According to such material testing machine, the initial starting rotational frequency of the motor is set according to a selected testing control mode. When the selected testing control mode is the stroke control mode based on the detection value of the displacement detector, a rotational frequency of the motor is obtained by calculation based on the strokes of the cylinder rod of the hydraulic cylinder inputted beforehand as testing parameter and stored in the storage unit. Since the motor is driven at the calculated rotational frequency through the inverter, it becomes possible further to reduce power consumption at the time of starting the motor.

In another preferred embodiment, the controller of the material testing machine is arranged to monitor a difference between a control signal of the flow control valve and a testing waveform during the testing, and when the difference exceeds a threshold set beforehand, to change the rotational frequency of the motor through the inverter.

According to such material testing machine, by monitoring the difference between the control signal of the flow control valve and the testing waveform, the rotational frequency of the motor can be controlled by inverter control according to testing situations, to realize a testing with increased stability while reducing power consumption.

Other features and advantages of the invention will be apparent from the following detailed description of the embodiments of the invention.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Figure 1:
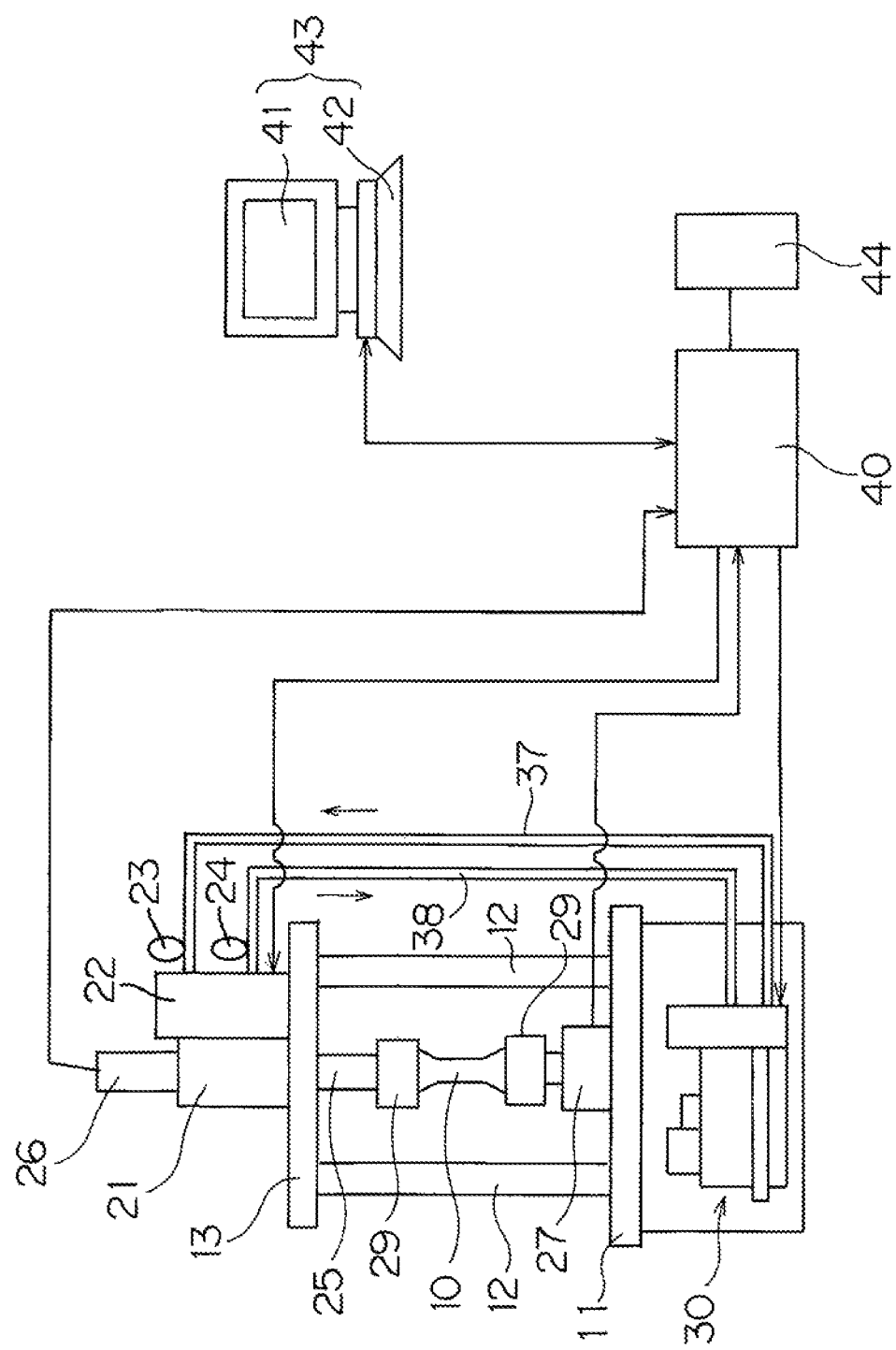
FIG. 1 is a schematic view of a material testing machine according to this invention.
Figure 2:
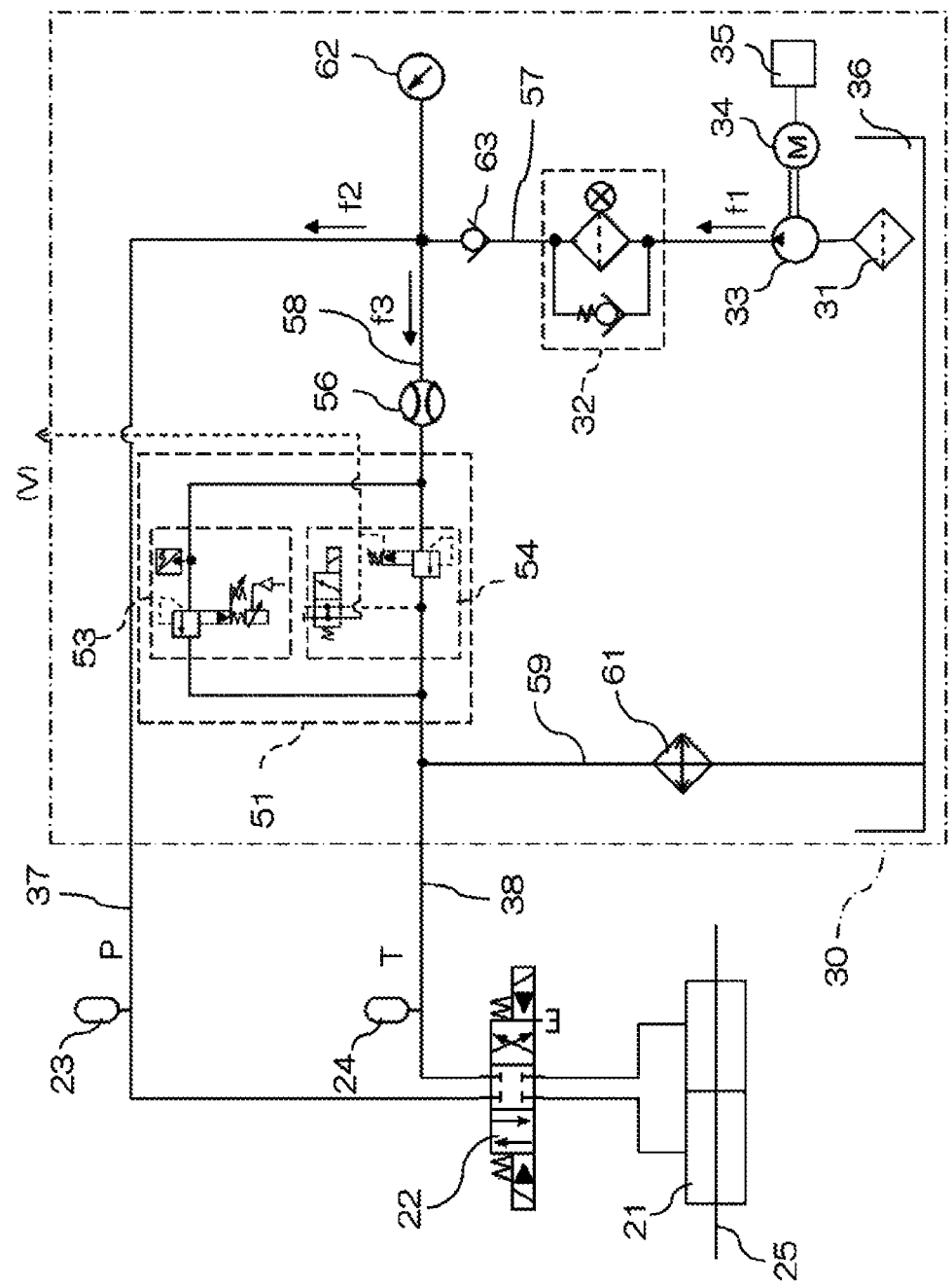
FIG. 2 is a hydraulic circuit diagram of the material testing machine according to this invention.
Figure 3:
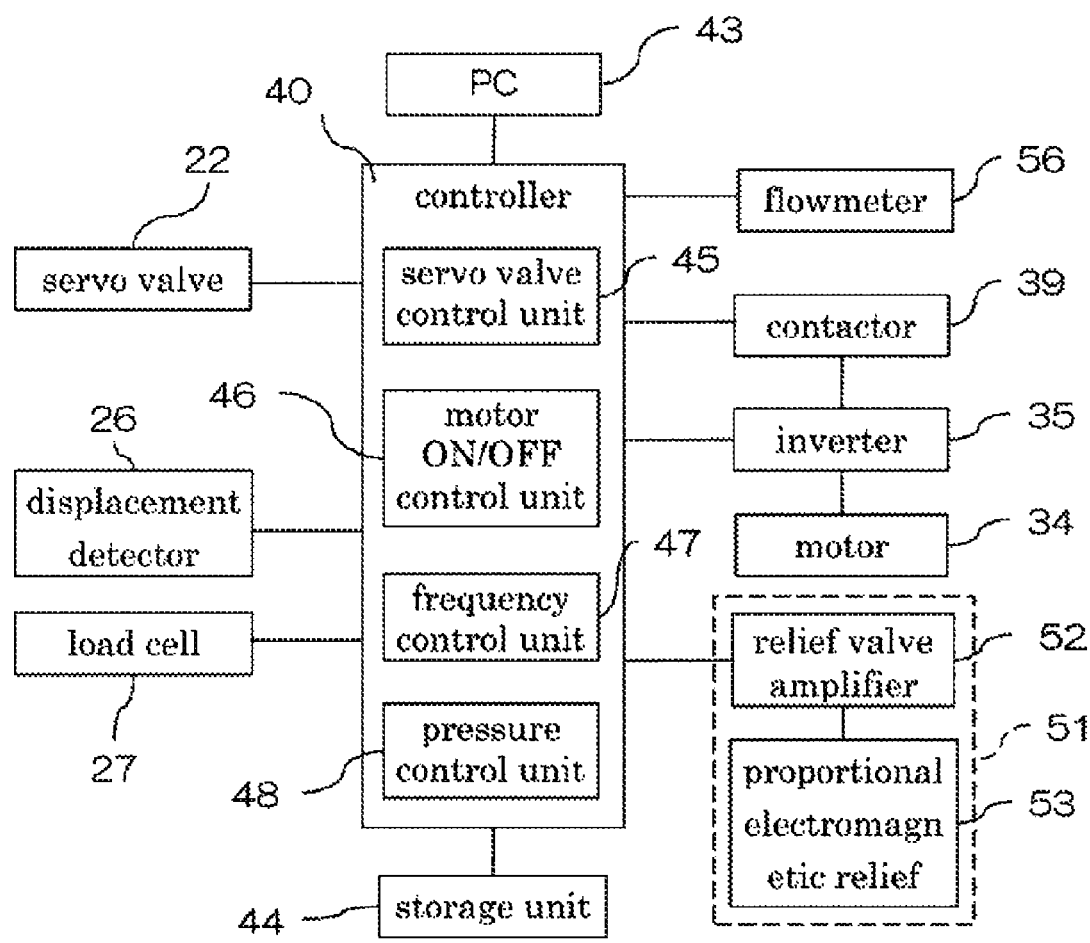
FIG. 3 is a block diagram showing a principal control system of the material testing machine according to this invention.

An embodiment of this invention will be described hereinafter with reference to the drawings. FIG. 1 is a schematic view of a material testing machine according to this invention. FIG. 2 is a hydraulic circuit diagram of this material testing machine. FIG. 3 is a block diagram showing a principal control system of the material testing machine.

This material testing machine includes a pair of columns 12 supported by a table 11, and a deck 13 supported by these columns 12. A hydraulic cylinder 21 is disposed on the deck 13 for applying a testing force to a specimen 10 serving as a test piece. This hydraulic cylinder 21 is connected to a servo valve 22 which determines a supply rate of hydraulic oil by amount of valve opening, and a displacement detector 26 which detects displacement of a cylinder rod 25 of the hydraulic cylinder 21. A gripper 29 is attached to the cylinder rod 25 of the hydraulic cylinder 21 for gripping an upper end of the specimen 10.

The table 11 has, mounted thereon, a load cell 27 acting as a testing force detector for detecting the testing force, and another gripper 29 for gripping a lower end of the specimen 10. A hydraulic pressure source 30 which supplies hydraulic oil for operating the hydraulic cylinder 21 is disposed below the table 11.

This material testing machine includes a controller 40 for controlling the entire apparatus, and a storage unit 44 for storing various data. The controller 40 is connected to a computer 43 having a display 41 and an input unit 42, and containing a ROM, a RAM, and a CPU which performs logical operations. The servo valve 22 noted above has its amount of opening controlled by control signals supplied from the controller 40. An output signal of the displacement detector 26 and an output signal of the load cell 27 are taken into the controller 40 at every predetermined time during an execution of material testing.

The hydraulic cylinder 21 is operable by the hydraulic oil supplied from the hydraulic pressure source 30. The hydraulic oil from the hydraulic pressure source 30 is supplied from a supply pipe line 37 to the hydraulic cylinder 21 through the servo valve 22. The hydraulic oil discharged from the hydraulic cylinder 21 is, after passing through the servo valve 22, returned to the hydraulic pressure source 30 through a return pipe line 38. The supply pipe line 37 has a P-side accumulator 23 mounted thereon, and the return pipe line 38 a T-side accumulator 24 mounted thereon. The P-side accumulator 23 and T-side accumulator 24 store pressures required for causing reciprocation of the cylinder rod 25, respectively.

The hydraulic pressure source 30 includes an oil tank 36 which stores the hydraulic oil, a hydraulic pump 33, a motor 34 for driving this hydraulic pump 33, and an inverter 35 for changing a rotational frequency of the motor 34. The motor 34 used here is a motor, such as an induction motor or a synchronous motor, rotatable by AC power supply, and with its rotational frequency changeable by control of the inverter 35.

A suction filter 31 is disposed at an admission port of a pipe line 57 which sucks the hydraulic oil from the oil tank 36 by operation of the hydraulic pump 33. A line filter 32 with a clogging indicator is disposed at a discharge port side of the hydraulic pump 33. The pipe line 57 includes a check valve 63 mounted thereon for preventing a reverse flow through the pipe line 57 of the hydraulic oil discharged from the hydraulic pump 33.

The pipe line 57 branches to the supply pipe line 37 which supplies the hydraulic oil to the hydraulic cylinder 21, and a release pipe line 58 which releases a superfluous part of the hydraulic oil to the oil tank 36. The release pipe line 58 has, arranged thereon, a pressure regulating mechanism 51, and a flowmeter 56 which measures a flow rate of the hydraulic oil having flowed into the release pipe line 58. A pipe branching opposite from the release pipe line 58 has a pressure gauge 62 attached thereto for enabling external monitoring of the pressure in this hydraulic circuit.

The pressure regulating mechanism 51 is provided for regulating the pressure in this hydraulic circuit from the oil tank 36 to the hydraulic cylinder 21, and has a construction including members, such as relief valves, for regulating the pressure of the hydraulic oil. This pressure regulating mechanism 51 includes a relief valve 54 with an electromagnetic selector valve capable of flow path switching between a vent (V) to the exterior and the oil tank 36, and a proportional electromagnetic relief valve 53 with a pressure sensor, which is connected to a bypass pipe line and capable of proportionally controlling the pressure in the hydraulic circuit in response to input voltage. The relief valve 54 with the electromagnetic selector valve switches the flow path of the hydraulic oil to the oil tank 36 at a no-load time. During a test execution with a load application, the pressure in the hydraulic circuit is controlled by the proportional electromagnetic relief valve 53. The proportional electromagnetic relief valve 53, as distinct from a throttle valve which changes the cross-sectional area of a pipe line, changes the pressure of the flowing hydraulic oil while maintaining the cross-sectional area of the pipe line constant.

The flowmeter 56 can output a detected flow rate externally of the hydraulic pressure source 30, the detected flow rate being inputted to the controller 40. This embodiment employs an ultrasonic flowmeter which, by contactlessly detecting the flow rate, causes no variation in the flow rate. The flowmeter 56 is disposed on the side of the release pipe line 58 closer to the hydraulic pump 33 than is the pressure regulating mechanism 51. Since the relief valve forming part of the pressure regulating mechanism 51 changes the pressure of the flowing hydraulic oil while maintaining the cross-sectional area of the pipe line constant, the flow rate of the hydraulic oil flowing through the release pipe line 58 is not influenced by pressure regulating action of the pressure regulating mechanism 51.

The hydraulic oil stored in the oil tank 36 is fed under pressure into the supply pipe line 37 by action of the hydraulic pump 33. Then, the hydraulic oil is accumulated by the P-side accumulator 23, and is fed in a state of constant pressure to the hydraulic cylinder 21 through the servo valve 22. The hydraulic oil fed from the hydraulic cylinder 21 to the return pipe line 38 flows through the servo valve 22 and T-side accumulator 24 and through the return pipe line 38 to be collected in the oil tank 36.

A superfluous part exceeding the flow rate required for testing of the hydraulic oil discharged from the hydraulic pump 33 is collected in the oil tank 36 by way of the release pipe line 58. In this embodiment, the pipe line from the return pipe line 38 to the oil tank 36 and the pipe line from the release pipe line 58 to the oil tank 36 merge into a common pipe line 59, thereby to simplify the piping. The hydraulic oil returned to the oil tank 36 is made to pass necessarily through one oil cooler 61, thereby to realize a construction which, though simple, can further reduce deterioration of the hydraulic oil.

The controller 40 includes, as functional constituents, a servo valve control unit 45 for controlling an amount of opening of the servo valve 22, a motor ON/OFF control unit 46 for giving ON/OFF signals of the motor 34 to a contactor 39, a frequency control unit 47 for giving control signals to the inverter 35 for setting a rotation frequency of the motor 34, and a pressure control unit 48 for giving a pressure regulating signal to a relief valve amplifier 52 which outputs an input voltage to the proportional electromagnetic relief valve 53.

In the material testing machine having the above construction, with the pair of grippers 29 gripping the opposite ends of the specimen 10, the cylinder rod 25 of the hydraulic cylinder 21 is made to reciprocate to apply a vibrating load to the specimen 10. Strokes of the reciprocation of the cylinder rod 25 in the hydraulic cylinder 21 at this time are detected by the displacement detector 26. The testing force applied to the specimen 10 at this time is detected by the load cell 27. As noted hereinbefore, the output signal of the displacement detector 26 and the output signal of the load cell 27 at this time are taken into the controller 40. A detection value of the flowmeter 56 is also taken into the controller 40.

Figure 4:
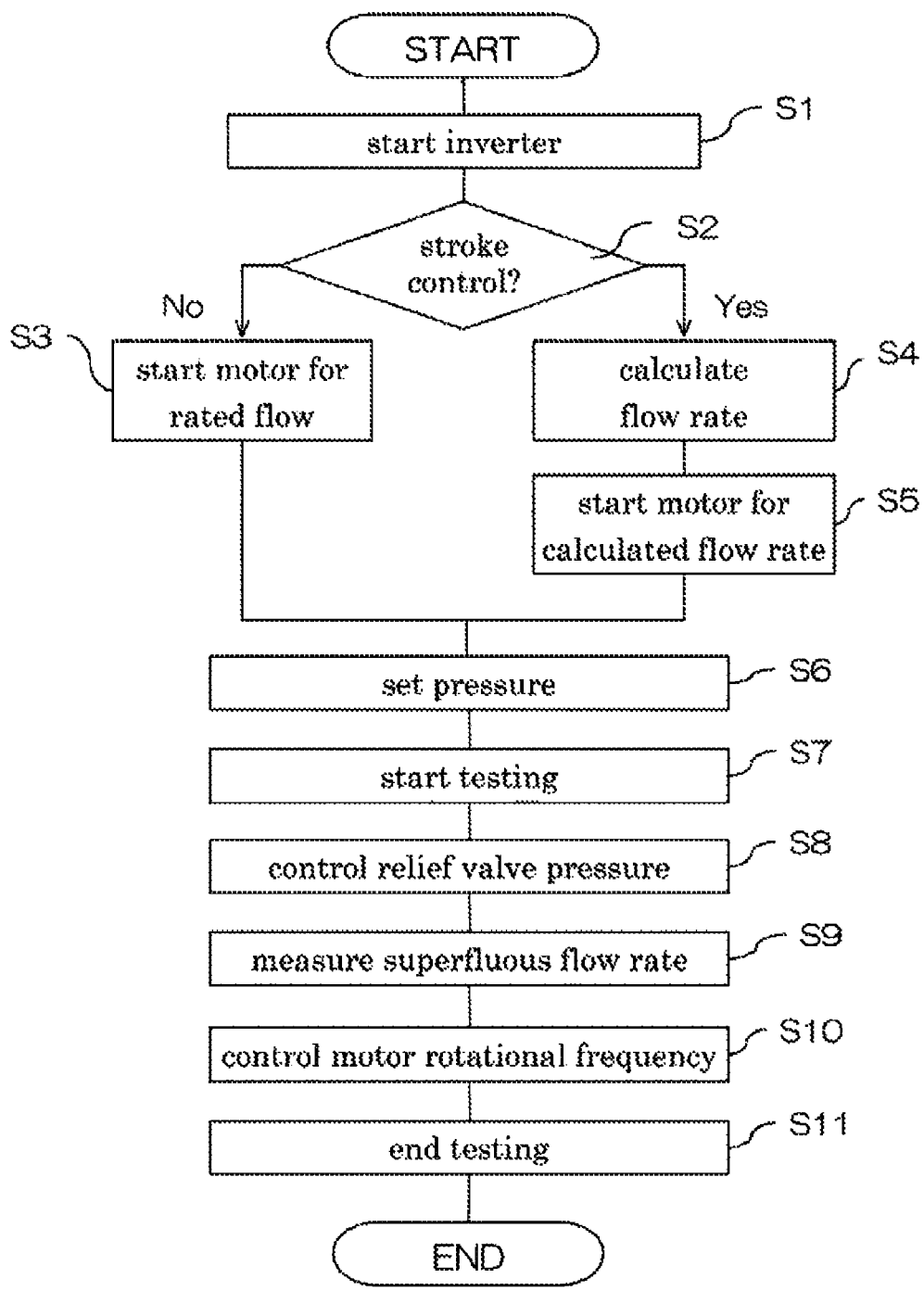
FIG. 4 is a flow chart illustrating a flow control of hydraulic oil during a material testing with the material testing machine according to this invention.

Next, an operation for adjusting the flow rate of the hydraulic oil when conducting a test with the above material testing machine will be described taking a fatigue test for example. FIG. 4 is a flow chart illustrating flow rate adjustment of hydraulic oil during a material testing with the material testing machine according to this invention.

When conducting a material testing of the specimen 10 as test piece with the material testing machine according to this invention, the first step taken is to start the inverter 35 which controls the motor 34 for driving the hydraulic pump 33 in the hydraulic pressure source 30 (step S1). Next, a determination is made whether a stroke control mode is selected as testing control mode for conducting the testing, or a different testing control mode is selected (step S2).

Here, the stroke control mode is a testing control mode which performs closed-loop control of the servo valve 22, with the strokes of the cylinder rod 25 of the hydraulic cylinder 21 detected by the displacement detector 26 serving as controlled variable. As a testing control mode other than the stroke control mode, this embodiment provides selection of a testing force control mode in which the controlled variable is the testing force applied to the specimen 10 and detected by the load cell 27. When a contact type extensometer for detecting elongation of the specimen 10 or a distortion meter affixed to the specimen 10 for detecting its distortion, for example, is added to the construction of the material testing machine to carry out tensile testing, it is possible to select a testing control mode in which an amount of displacement due to elongation or distortion serves as controlled variable.

When the stroke control mode is selected, a discharge rate D (L/min) of the hydraulic oil required of the hydraulic pump 33 is derived from equation (1) set out below, where a (mm) is an amplitude of the reciprocating strokes of the cylinder rod 25, f (Hz) is a frequency, A (mm$^2$) is the cross-section area of the hydraulic cylinder 21 which is known from the specifications, and c1 is a coefficient determined from the characteristics of the hydraulic pressure source 30 and servo valve 22 (step S4). In the stroke control mode, values of amplitude a of the reciprocating strokes of the cylinder rod 25 and frequency f are beforehand inputted through the input unit 42 and stored in the storage unit 44 as testing parameters.

$$D = c1 \cdot f \cdot a \cdot A \quad (1)$$

Discharge rate D of the hydraulic pump 33 is in a proportional relation with the rotational frequency of the motor 34 which drives the hydraulic pump 33. Therefore, the rotational frequency of the motor 34 is calculated from discharge rate D derived from equation (1), and the motor 34 is started at the calculated rotational frequency which realizes the required flow rate (step S5).

On the other hand, when a testing control mode other than the stroke control mode is selected (step S2), the motor 34 is started at a rotational frequency for discharging the hydraulic oil in a rated flow of the hydraulic pump 33 (step S3). This is because, unlike the case of the stroke control mode, it is difficult to predict a required flow at an initial stage of the hydraulic oil by calculation from the mechanical dimensions of the hydraulic cylinder 21 and the testing conditions determined beforehand. In the state where the motor 34 is started (steps S3, S5), the servo valve 22 in the material testing machine is closed, so that the hydraulic oil drawn from the oil tank 36 by the hydraulic pump 33 flows through the release pipe line 58 and common pipe line 59 to be collected again in the oil tank 36.

Next, a pressure value is set for operating the pressure regulating mechanism 51 to bring the pressure in the hydraulic circuit to a predetermined pressure (step S6). Preparations for the testing are completed such as by attaching the specimen 10 to the grippers 29. The pressure value at this time may be any value appropriate to the testing which is set through the input unit 42. Subsequently, the testing is started by operating the servo valve control unit 45 to control the servo valve 22 to supply the hydraulic oil to the hydraulic cylinder 21 through the supply pipe line 37 (step S7). This moves the cylinder rod 25 to apply vibration to the specimen 10 supported by the grippers 29.

The strokes of reciprocation of the cylinder rod 25 in the hydraulic cylinder 21 at this time are detected by the displacement detector 26. The testing force applied to the specimen 10 at this time is detected by the load cell 27. In the stroke control mode, for example, the open-close state of the servo valve 22 is controlled to bring the reciprocating strokes of the cylinder rod 25 to a set value. In the testing force control mode, the open-close state of the servo valve 22 is controlled to bring the testing force applied to the specimen 10 to a predetermined value.

The controller 40 reads a degree of the testing force applied to the specimen 10 and detected by the load cell 27, and based on the degree of the testing force read, calculates the pressure of the hydraulic oil to be supplied to the hydraulic cylinder 21. This calculation is performed as follows.

A supply pressure P (MPa) of the hydraulic oil to the hydraulic cylinder 21 is expressed by the following equation (2), where L (kN) is the testing force applied to the specimen 10, and c2 is a coefficient:

$$P = c2 \cdot L \quad (2)$$

Thus, this equation (2) enables calculation of the supply pressure of the hydraulic oil to the hydraulic cylinder 21.

Once the supply pressure of the hydraulic oil to the hydraulic cylinder 21 is calculated, the pressure control unit 48 in the controller 40 is operated to control the proportional electromagnetic relief valve 53 through the relief valve amplifier 52 (step S8) to adjust the pressure in the hydraulic circuit, ie the supply pressure of the hydraulic oil to the hydraulic cylinder 21.

When a certain period of time elapses after start of this material testing, shape variations of the specimen 10 will become stable, which in turn stabilizes detection signals of stroke displacement of the cylinder rod 25 detected by the displacement detector 26 and detection signals of the testing force detected by the load cell 27. In this state, the flowmeter 56 measures a flow rate of the hydraulic oil flowing into the release pipe line 58. Flow rate f3 measured is transmitted through the controller 40 to the computer 43 (step S9).

The following equation (3) expresses a relation between flow rates f1, f2 and f3, where f1 is a flow rate of the hydraulic oil drawn from the oil tank 36 and discharged from the hydraulic pump 33, and f2 is a flow rate of the hydraulic oil flowing into the supply line 37 to the hydraulic cylinder 21 (see FIG. 2):

$$f3 = f1 - f2 \quad (3)$$

Flow rate f1 can be obtained by calculation at any time as a flow rate during an execution of testing, by using equation (1) given hereinbefore, and changing amplitude a (mm) of the cylinder rod 25 based on the detection value of the displacement detector 26.

Flow rate f3 measured by the flowmeter 56 is a superfluous flow rate which is not consumed as the load applied to the specimen 10 but will be lost as thermal energy. Therefore, the closer to zero flow rate f3 is reduced, the hydraulic pressure source 30 can be operated with the higher efficiency and less energy loss. When the stroke control mode is selected as testing control mode, the initial drive rotational frequency of the motor 34 is calculated based on the required flow rate derived from equation (1) given hereinbefore. Thus, a difference between the required flow rate obtained by calculation and an actually required flow rate corresponds to flow rate f3. In this invention, therefore, the control signal for controlling the rotational frequency of the motor 34 is changed so as to make the flow rate f3 measured by the flowmeter 56 approach zero (step S10). This improves the energy efficiency of the hydraulic pressure source 30.

Flow rate f3 measured by the flowmeter 56 mounted on the release pipe line 58 becomes zero also when the rotational frequency of the motor 34 is insufficient so that all the hydraulic oil discharged from the hydraulic pump 33 and supplied from the supply line 37 to the hydraulic cylinder 21 falls short of the flow rate required for the testing. It is therefore preferable, in the rotational frequency control of the motor 34 which reduces flow rate f3 close to zero, to set a target value of flow rate f3 not to zero, but to a minimum value within a range that enables the testing to be carried out normally with set testing conditions. In this embodiment, taking into consideration operation influences on the servo valve 22 from the specifications of the hydraulic pump 33 and an amplitude waveform of the cylinder rod 25, a minimum value permissible as energy loss within a range that enables the testing to be carried out normally is obtained experimentally, and is set as a target value of flow rate f3. And a command signal of the rotational frequency of the motor 34 is changed using the CPU of the computer 43 so that the measurement value of the flowmeter 56 will approach this target value.

In this embodiment, from the amplitude of the strokes of the cylinder rod 25 set beforehand and the detection value of the displacement detector 26, and using equation (1), flow rate f1 is calculated as discharge rate D of the hydraulic pump 33 required for testing. The rotational frequency of the motor 34 which drives the hydraulic pump 33 is calculated from the discharge rate obtained. And in response to a part exceeding the target value of the flow rate f3 measured by the flowmeter 56, the frequency control signal given to the inverter 35 from the frequency control unit 47 of the controller 40 is changed by performing an arithmetic operation using the CPU of the computer 43 to reduce the rotational frequency of the motor 34 calculated earlier.

Monitoring of the superfluous flow rate by the flowmeter 56, and changing of the rotational frequency of the motor 34 based on the flow rate measured by the flowmeter 56, are repeated at regular time intervals until the testing is completed. When the required material testing is completed (step S11), the process is ended.

In this embodiment, not only the monitoring of the superfluous flow rate by the flowmeter 56, but also monitoring can be conducted, with the strokes detected by the displacement detector 26 being transmitted from the controller 40 to the computer 43, of a difference between the control signal of the servo valve 22 which controls the flow rates of the hydraulic oil flowing into the hydraulic cylinder 21 and flowing out of the hydraulic cylinder 21, and the testing waveform. That is, when the difference between the control signal and the testing waveform exceeds a threshold set beforehand, which indicates a probability of large variations in the value of flow rate f2 through the supply line 37, the rotational frequency of the motor 34 may be changed through the inverter 35 based on the difference, separately from the change, repeated at regular time intervals, of the rotational frequency of the motor 34 based on the flow rate measured by the flowmeter 56.

According to the material testing machine in this embodiment, as described above, the flowmeter 56 is mounted on the release pipe line 58, and based on the flow rate measured by the flowmeter 56, a change is made of the rotational frequency of the motor 34 determined based on the strokes of the cylinder rod 25 of the hydraulic cylinder 21 detected by the displacement detector 26. This prevents the hydraulic oil not to be used for loading from being wastefully discharged from the hydraulic pump 33, thereby to reduce deterioration of the hydraulic oil and to improve the energy efficiency of the hydraulic pressure source 30. It is therefore possible to reduce drastically power consumption in conducting material testing.

In the embodiment described above, the initial starting rotational frequency of the motor 34 is set according to a selected testing control mode (step S2-step S5). When the selected testing control mode is the stroke control mode based on the detection value of the displacement detector 26, a rotational frequency of the motor 34 which realizes a flow rate of hydraulic oil required for testing is obtained by calculation based on the strokes of the cylinder rod 25 of the hydraulic cylinder 21 inputted beforehand as testing parameter and stored in the storage unit 44. Since what is necessary is just to drive the motor 34 at the calculated rotational frequency through the inverter 35, it is unnecessary to raise the rotational frequency of the motor 34 to rated capacity. It also becomes possible to reduce wasteful energy consumption at the time of starting the motor 34.

This invention may be embodied in other specific forms without departing from the spirit or essential attributes thereof and, accordingly, reference should be made to the appended claims, rather than to the foregoing specification, as indicating the scope of the invention.

This application claims priority benefit under 35 U.S.C. Section 119 of Japanese Patent Application No. 2013-254035 filed in the Japanese Patent Office on Dec. 9, 2013, the entire disclosure of which is incorporated herein by reference.

What is claimed is:

1. A material testing machine for conducting a material testing by applying a testing force to a test specimen, the machine comprising a hydraulic cylinder, a hydraulic pressure source for supplying hydraulic oil to the hydraulic cylinder, and a flow control valve for controlling flow rates of the hydraulic oil which flows into the hydraulic cylinder and out of the hydraulic cylinder; wherein
the hydraulic pressure source includes:
a pump for feeding the hydraulic oil in a tank to the hydraulic cylinder;
a motor for driving the pump;
an inverter connected to the motor for changing a rotational frequency of the motor;
a release pipe line having mounted thereon a pressure regulating mechanism for regulating a pressure in a hydraulic circuit, the release pipe line branching from a pipe line which supplies the hydraulic oil from the tank through the pump to the hydraulic cylinder, for releasing a superfluous part of the hydraulic oil discharged from the pump;
a flowmeter mounted on the release pipe line for measuring a flow rate of the hydraulic oil flowing into the release pipe line;
a controller for controlling the rotational frequency of the motor through the inverter based on a measurement value of the flowmeter; and
wherein the pressure regulating mechanism includes a relief valve with an electromagnetic selector valve that is capable of flow path switching between a vent to the exterior and an oil tank.

2. The material testing machine according to claim 1, further comprising:
a displacement detector for detecting strokes of a cylinder rod of the hydraulic cylinder when conducting the material testing by applying the testing force to the test specimen;
an input unit for setting beforehand the strokes of the cylinder rod of the hydraulic cylinder when conducting the material testing by applying the testing force to the test specimen; and
a storage unit for storing the strokes of the cylinder rod of the hydraulic cylinder inputted by the input unit;
wherein the controller is arranged to set an initial starting rotational frequency of the motor in response to whether a testing control mode selected at a time of starting the testing is a stroke control mode based on a detection value of the displacement detector or a control mode other than the stroke control mode, and when the testing control mode selected at the time of starting the testing is the stroke control mode, to start the motor at a rotational frequency according to a discharge rate of the pump calculated based on the strokes of the cylinder rod of the hydraulic cylinder stored in the storage unit.

3. The material testing machine according to claim 1, wherein the controller is arranged to monitor a difference between a control signal of the flow control valve and a testing waveform during the testing, and when the difference exceeds a threshold set beforehand, to change the rotational frequency of the motor through the inverter.

4. The material testing machine according to claim 2, wherein the controller is arranged to monitor a difference between a control signal of the flow control valve and a testing waveform during the testing, and when the difference exceeds a threshold set beforehand, to change the rotational frequency of the motor through the inverter.

5. The material testing machine according to claim 1, wherein the pressure regulating mechanism further includes a proportional electromagnetic relief valve with a pressure sensor, which is connected to a bypass pipe line and is capable of proportionally controlling pressure in the hydraulic circuit in response to input voltage.

6. The material testing machine according to claim 5, wherein the relief valve with the electromagnetic selector valve is capable of switching the flow path of the hydraulic oil to an oil tank at a no-load time.

7. The material testing machine according to claim 6, wherein during a test execution with a load application, the hydraulic circuit has a pressure that is controlled by the proportional electromagnetic relief valve.

8. The material testing machine according to claim 7, wherein the proportional electromagnetic relief valve is capable of changing pressure of flowing hydraulic oil while maintaining the cross-sectional area of the bypass pipe line constant.

9. The material testing machine according to claim 1, wherein the flowmeter is disposed on the side of the release pipe line closer to the hydraulic pump than is the pressure regulating mechanism.

10. The material testing machine according to claim 1, wherein the release pipe line is connected to the common pipe line that is connected to the return pipe line for returning oil returned from the cylinder to the tank, and an oil cooler is provided in the common pipe line.

* * * * *